United States Patent [19]

Klem et al.

[11] Patent Number: 5,726,300
[45] Date of Patent: Mar. 10, 1998

[54] PROCESS FOR THE SYNTHESIS OF OLIGONUCLEOTIDES AND ANALOGS WITH LOW WATER OXIDATION STEP

[75] Inventors: Robert E. Klem, San Luis Obispo; William B. Marvin, Los Osos; Timothy A. Riley, Grover City, all of Calif.

[73] Assignee: Genta Incorporated, San Diego, Calif.

[21] Appl. No.: 260,392

[22] Filed: Jun. 15, 1994

Related U.S. Application Data

[63] Continuation of Ser. No. 37,718, Mar. 24, 1993, abandoned, which is a continuation of Ser. No. 605,790, Oct. 26, 1990, abandoned.

[51] Int. Cl.$^6$ .......................... C07H 21/00; C07H 21/04
[52] U.S. Cl. ........................... 536/25.34; 536/25.3
[58] Field of Search ..................... 536/25.3, 25.34

[56] References Cited

U.S. PATENT DOCUMENTS

| | | | |
|---|---|---|---|
| 4,415,732 | 11/1983 | Caruthers et al. | 536/26.5 |
| 4,458,066 | 7/1984 | Caruthers et al. | 536/25.34 |
| 4,469,863 | 9/1984 | Ts'o et al. | 536/24.5 |
| 4,500,707 | 2/1985 | Caruthers et al. | 536/25.34 |
| 4,668,777 | 5/1987 | Caruthers et al. | 536/26.5 |
| 4,725,677 | 2/1988 | Köster et al. | 536/25.34 |
| 4,923,901 | 5/1990 | Köster et al. | 521/53 |

OTHER PUBLICATIONS

Beaucage et al., "Advances in the Synthesis of Oligonucleotides by the Phosphoramidite Approach," *Tetrahedron*, 48(12), 2223–2311 (1992).

Pon, "Enhanced Coupling Efficiency Using 4–Dimethylaminopyridine (DMAP) and Either Tetrazole, 5–(o–Nitrophenyl)tetrazole, or 5–(p–Nitrophenyl)tetrazole in the Solid Phase Synthesis of Oligoribonucleotides by the Phosphoramidite Procedure," *Tetrahedron Letters*, 28(32), 3643–3646 (1987).

Ogilvie et al., "The Synthesis of Phosphite Analogues of Ribonucleotides," *Tetrahedron Letters*, 21, 4145–4148 (1980).

Fourrey et al., "Improved Procedure for the Preparation of Deoxynucleoside Phosphoramidites: Arylphosphoramidites as New Convenient Intermediates for Oligonucleotide Synthesis," *Tetrahedron Letters*, 25(40), 4511–4514 (1984).

Windholz et al. (eds.), *The Merck Index*, 9th Ed., Merck & Co., Rahway, NJ, 1976, pp. 661–662 only.

Hogrefe, "Oligonucleotide Trihaloethyl Phsophotriesters: Assignment of Configureation and Utilization in Syntheses via the Phosphordichloridite Scaverngin Approach," Ph.D. Thesis, Northwestern University, Evanston, Illinois, Jun. 1987, Abstract, and pp. 80 and 87–88 only.

"Directory of Chemical Products for DNA/RNA Synthesis, Peptide Synthesis, Protein Sequencing and 2–D Electrophoresis," Millipore Corporation, Bedford, MA, Oct., 1991, p. 15 only.

Sarin et al., "Inhibition of Acquired Immunodeficiency Syndrome Virus by Oligodeoxynucleoside Methyl Phosphonates," *Proc. Nat. Acad. Sci. USA*, 85(20), 7448–7451 (1988).

Agrawal et al., "Oligodeoxynucleoside Methyl Phosphonates: Synthesis and Enzymatic Degradation," *Tetrahedron Letters*, 28(31), 3539–3542 (1987).

*Primary Examiner*—Gary E. Hollinden
*Assistant Examiner*—L. Eric Crane
*Attorney, Agent, or Firm*—Lyon & Lyon

[57] ABSTRACT

Methods of synthesizing oligomers using low water oxidizer reagents which result in high coupling efficiencies are provided. These methods are suitable for larger scale preparations of methylphosphonate oligomers.

28 Claims, 1 Drawing Sheet

PROCESS FOR THE SYNTHESIS OF OLIGONUCLEOTIDES AND ANALOGS WITH LOW WATER OXIDATION STEP

This application is a continuation of U.S. Ser. No. 08/037,718, filed Mar. 24, 1993, now abandoned, which is a continuation of U.S. Ser. No. 07/605,790, filed Oct. 26, 1990, now abandoned.

BACKGROUND OF THE INVENTION

The present invention is directed to an improved process of synthesizing oligomers.

Methods for the chemical synthesis of oligomers, and in particular, oligomers composed of deoxynucleosides have been developed. These methods include the phosphotriester method and phosphite triester method. These syntheses may be conducted in solution, yielding dimers which are then purified chromatographically; the purified dimers may be linked together to give a tetramer and so forth. Preferably, a solid phase method is employed, using a 5'-O-protected nucleoside attached to a solid support. In the solid phase method, a 5'-O-protected nucleoside is attached to a solid support and an oligomer is synthesized by chain assembly using alternating terminal 5'-deprotection reactions and coupling reactions. In both the solution and solid phase synthesis methods, excess reagent is added to drive the reaction to completion and unreacted components are removed by washing of the support with an appropriate solvent. Cycles of deprotection and coupling are continued until the desired oligomer length is obtained. Then, the oligomer is cleaved from the support, protecting groups are removed, and the deprotected oligomer is purified. Suitable solid supports for those synthesis methods include silica gel, controlled pore glass beads (CPG) and polystyrene. (See, in general, Gait, M. S., *Oligonucleotide Synthesis A Practical Approach*, IRL Press (1985)).

Instruments for the solid phase synthesis of oligomers are commercially available. The instructions provided by the manufacturers of these instruments include preferred ratios of reactants and reagents for oligomer synthesis. In the coupling step, large excesses of monomer and activator of monomer have been recommended. In the oxidation step, the recommended oxidizer reagent contains large amount (about 2% to about 25% or greater) of water.

SUMMARY OF THE INVENTION

The present invention is directed to improved processes for the synthesis of oligomers.

Among other factors, the present invention is based on our finding that this improved synthesis process which uses a low water oxidizer reagent in the oxidizing step allows for synthesis of oligomers in relatively large amounts (about 15 μmoles or greater) with high coupling efficiencies (about 95% or more), but allows use of significantly lower equivalent amounts of nucleoside monomer and activator in the coupling step.

In one aspect the present invention is directed to a process of forming an internucleoside linkage between a 5'-oxygen of a first nucleoside and a 3'-oxygen of a second nucleoside (or monomer, see FIG. 1) wherein the first nucleoside has a blocking group attached to its 5'-oxygen and is linked by its 3'-oxygen to a support or to another nucleoside or to an oligomer by a 5'-internuceloside linkage; and the second nucleoside has a blocking group attached to its 5'-oxygen and a coupling group of the following formula attached to its 3'-oxygen:

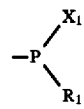

wherein $X_1$ is halogen or substituted amino; and $R_1$ is alkyl, aryl, optionally substituted alkoxy or optionally substituted aryloxy. The process comprises treating the first nucleoside under deblocking conditions to remove the blocking group from the 5'-oxygen and generate a free 5'-hydroxyl group. Then, contacting under activating and coupling conditions, the deblocked first nucleoside and the second nucleoside in the presence of an activator, so that the first nucleoside and the second nucleoside are coupled by an internucleoside linkage having a trivalent phosphorus group. The trivalent phosphorus of the internucleoside linkage is oxidized to a pentavalent phosphorus under oxidizing conditions which include a low water oxidizer reagent which comprises about 2% or less water, but at least about 1 to about 5 equivalents water per equivalent first nucleoside, and preferably from about 0.1% to about 0.5% water. The oxidizer reagent comprises a suitable oxidizing agent, preferably about 100 mM to 200 mM oxidizing agent, and at least about 1 to about 5 equivalents oxidizing agent per equivalent first nucleoside. Suitable oxidizing agents include iodine ($I_2$). Following the oxidizing step is a capping step which caps unreacted 5'-hydroxyl groups on the first nucleoside to render them unreactive. In a preferred aspect, in the coupling step the second nucleoside or monomer is present in a ratio of about 1 to about 5 equivalents, more preferably from about 1.2 to about 3 equivalents, of second nucleoside per equivalent of first nucleoside. Especially preferred are ratios of about 1.5 to about 2 equivalents of second nucleoside per equivalent first nucleoside. The above process is repeated to add additional monomers to the growing oligomer chain until an oligomer of desired chain length is obtained. In the solid phase process, when synthesis of the oligomer has been completed, the oligomer is cleaved from the solid support using conventional procedures.

Synthesis of methylphosphonate oligomers using conventionally recommended reagent ratios and oxidizer reagents has resulted in relatively poor overall coupling efficiencies and, thus, in unsatisfactory yields, particularly in preparations of about 15 μmoles or greater. In particular, we have surprisingly found this improved process allows for the large scale production of methylphosphonate oligomers in improved yields while requiring significantly less monomer and activator. Use of decreased amounts of monomer is particularly advantageous, allowing for the more economical synthesis of oligomers due to the expense of monomer.

Definitions

As used herein, the following terms have the following meanings, unless expressly stated to the contrary:

The term "nucleoside" includes a nucleosidyl moiety or unit and is used interchangeably therewith.

The term "nucleotide" refers to a subunit of a nucleic acid consisting of a phosphate group, a sugar and a nitrogen containing base. In RNA, the sugar is ribose. In DNA, it is a 2-deoxyribose. The term also includes analogs of such subunits.

The terms "nucleotide multimer" refers to a chain of nucleotides linked by internucleoside phosphate linkages, or analogs thereof.

An "oligonucleotide" is a nucleotide multimer generally about 3 to about 100 nucleotides in length, but which may be greater than 100 nucleotides in length. They are usually considered to be synthesized from nucleotide monomers.

A "deoxyribooligonucleotide" is an oligonucleotide consisting of deoxyribonucleotide monomers.

A "polynucleotide" refers to a nucleotide multimer generally about 100 nucleotides or more in length. These are usually of biological origin or are obtained by enzymatic means.

A "monomeric unit" refers to a unit of either a nucleotide reagent or a non-nucleotide reagent of the present invention, which the reagent contributes to a polymer.

A "non-nucleotide monomeric unit" refers to a monomeric unit which does not significantly participate in hybridization of an oligomer. Such monomeric units must not, for example, participate in any significant hydrogen bonding with a nucleotide, and optionally include groupings capable of interacting after hybridization of oligomer to the target sequence, e.g. such as crosslinking alkylation, intercalating and chelating agents.

An "oligonucleotide/non-nucleotide multimer" is a multimer generally of synthetic origin having less than 100 nucleotides, but which may contain in excess of 200 nucleotides and which contains one or more non-nucleotide monomeric units.

The term "oligomer" refers to oligonucleotides, nonionic oligonucleoside alkyl- and aryl-phosphonate analogs, phosphorothioate analogs of oligonucleotides, phosphoamidate analogs of oligonucleotides, neutral phosphate ester oligonucleotide analogs, such as phosphotriesters and other oligonucleotide analogs and modified oligonucleotides, and also includes nucleotide/non-nucleotide polymers. The term also includes nucleotide/non-nucleotide polymers wherein one or more of the phosphorous group linkages between monomeric units has been replaced by a non-phosphorous linkage such as a formacetal linkage, a sulfamate linkage, or a carbamate linkage.

The term "alkyl- or aryl-phosphonate oligomer" refers to nucleotide/non-nucleotide polymers) having internucleoside (or intermonomer) phosphorus group linkages wherein at least one alkyl- or aryl- phosphonate linkage replaces a phosphodiester linkage.

The term "methylphosphonate oligomer" (or "MP-oligomer") refers to nucleotide oligomers (or nucleotide/non-nucleotide polymer) having internucleoside (or intermonomer) phosphorus group linkages wherein at least one methylphosphonate internucleoside linkage replaces a Phosphodiester internucleoside linkage.

In some of the various oligomer sequences listed herein "p" in, e.g., as in ApA represents a phosphate diester linkage, and "p" in, e.g., as in CpG represents a methylphosphonate linkage. Certain other sequences are depicted without the use of p or p to indicate the type of phosphorus diester linkage. In such occurrences, A as in ATC indicates a phosphate diester linkage between the 3'-carbon of A and the 5' carbon of T, whereas A, as in ATC or ATC indicates a methylphosphonate linkage between the 3'-carbon of A and the 5'-carbon of T or T.

The term "non-adverse conditions" describes conditions (of reaction or synthesis) which do not substantially adversely affect the oligomer skeleton and its sugar, and base components, nor the solid support. One skilled in the art can readily identify functionalities, coupling methods, deblocking and deprotection procedures and cleavage conditions which meet these criteria.

The term "deblocking conditions" describes the conditions used to remove the blocking (or protecting) group from the 5'-OH group on a ribose or deoxyribose group.

The term "deprotecting conditions" describes the conditions used to remove the protecting groups from the nucleoside bases.

The term to "cap" or "capping" refers to a step in the reaction cycle in which any 5'-hydroxyl groups of the first nucleoside (of a particular reaction cycle) that failed to condense (i.e. react) with the activated coupling group of the second nucleoside of that reaction cycle) are blocked, rendering them unreactive in further reaction cycles.

The term "loading" refers to the amount of nucelosidyl moiety (or nucleoside) which is coupled or linked (by a linking mnoiety) to a support or the polymeric moiety of a polymeric reagent and is typically expressed in μmoles nucleoside per gram support.

The term "support" refers to a solid particulate material to which a nucleoside is linked and from which an oligomer can be synthesized. Supports used in synthesizing oligomers are typically substantially inert and nonreactive with the reagents used in the synthesis of oligomers.

DETAILED DESCRIPTION OF THE INVENTION

Figure 1:
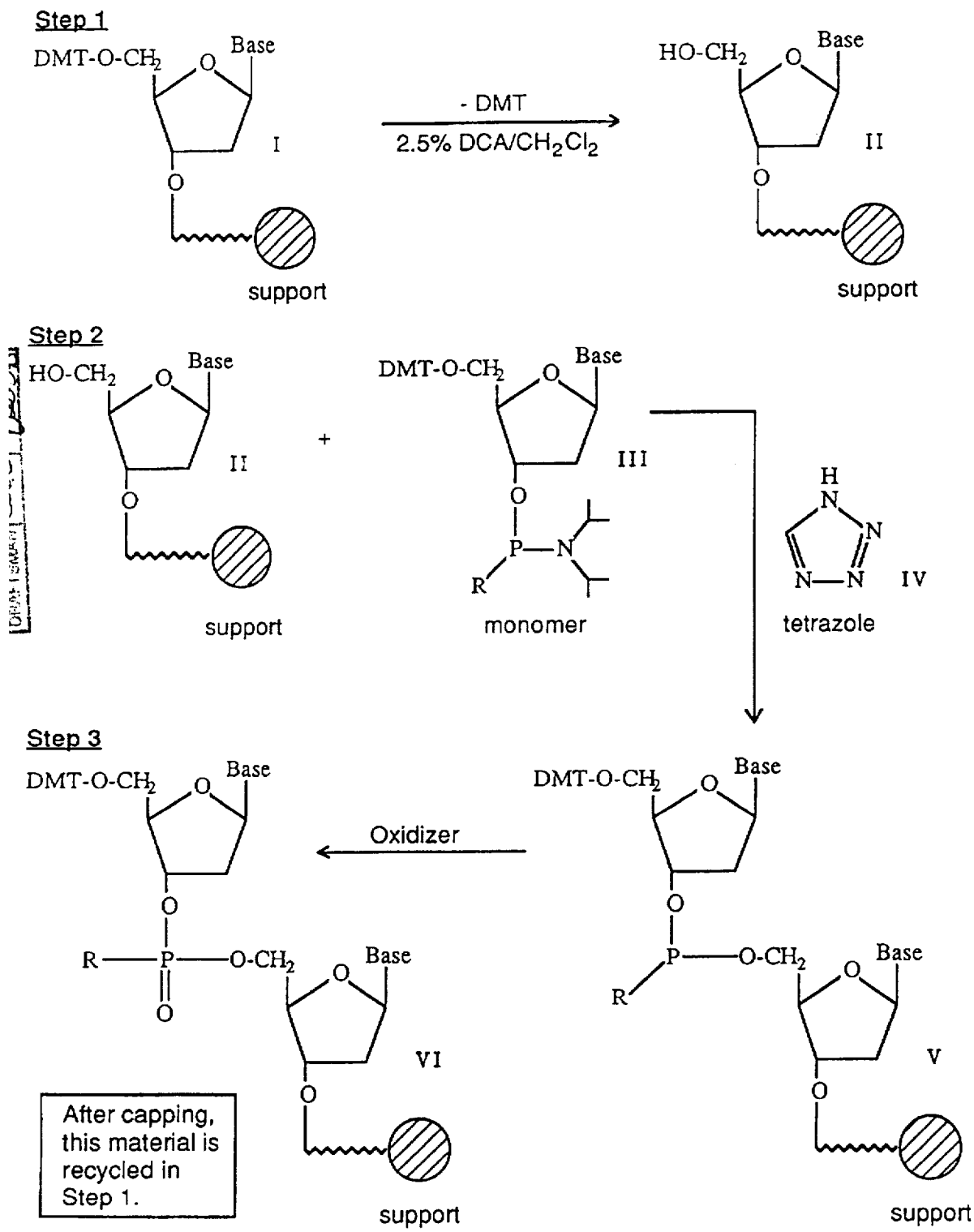
FIG. 1 depicts a general reaction scheme for the solid phase synthesis of oligomers according to the process of the present invention.

The present invention is directed to improved processes for synthesizing oligomers which comprise nucleoside monomeric units coupled by phosphorus-containing internucleoside linkages.

GENERAL REACTION SCHEME

In a general aspect, the present invention is directed to an improved process of forming an internucleoside linkage between a 5'-oxygen of a first nucleoside and a 3'-oxygen of a second nucleoside which uses a low water oxidizer reagent in the oxidizing step. The first nucleoside preferably has a blocked 5'-hydroxyl group and has at a 3'-carbon either a protected hydroxy group or preferably is linked by a 3'-oxygen to a solid support, or is linked by the 3'-oxygen to a phosphorous-containing group which is linked to the 5'-oxygen of another nucleoside which may be part of an oligomer. Preferably, the other nucleoside or oligomer is linked to a solid support. The second nucleoside has a blocking group attached to its 5'-oxygen and a coupling group attached to its 3'-oxygen, which coupling group preferably comprises:

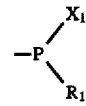

wherein $X_1$ is halogen or substituted amino and $R_1$ is alkyl, aryl, optionally substituted alkoxy or optionally substituted aryloxy.

The basic solid phase process of forming a phosphorous-containing internucleoside linkage according to the present invention is depicted in FIG. 1 and includes four steps: (a) deblocking of the 5'-hydroxyl of the first nucleoside; (b) adding the second nucleoside (or "monomer" in FIG. 1) to the reaction mixture having first nucleoside in the presence of an activator under coupling and activating conditions, so that the second nucleoside "couples" or "condenses" with the first nucleoside to give an internucleoside linkage having a trivalent phosphorus group; (c) oxidizing the trivalent phosphorus group to a pentavalent phosphorus group using a low water oxidizer reagent; and (d) capping to block unreacted (or uncoupled) 5'-hydroxyl groups on the first nucleoside.

Thus, in one aspect, the present invention is directed to a process for the preparation of deoxyribonucleoside phosphate or phosphonate esters of the formula

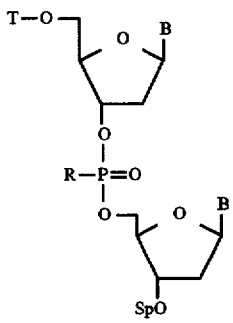 (I)

wherein T is a blocking group for a primary hydroxyl group; B is a base; R is hydroxy, alkyl, aryl, optionally substituted alkoxy, or optionally substituted aryloxy; and Sp is a support or a nucleoside 5'-phosphorus ester of the formula

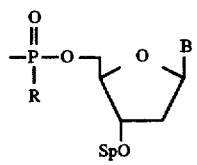 (II)

wherein R and Sp are defined as in connection with formula (I); wherein said blocked first nucleoside is deblocked to give a first nucleoside of the formula:

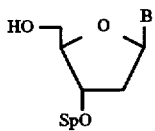 (III)

which is reacted with a second nucleoside of the formula

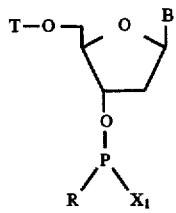 (IV)

wherein $X_1$ is halogen or substituted amino, in the presence of an activator to give a compound of the formula:

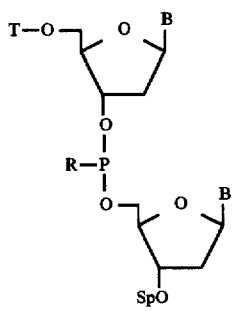 (V)

which is then oxidatively converted to a compound of formula I in the presence of a low water oxidizer agent which comprises about 2% or less water and at least about 1 to about 5 equivalents water per equivalent first nucleoside, preferably from about 0.1% to about 0.5% water.

(a) The Deblocking Step

This step involves treating the first nucleoside to remove the blocking group to give a 5'-hydroxyl which is capable of reacting with the coupling group of the second nucleoside. The blocking group is preferably di-(p-anisoyl) phenylmethyl ("dimethoxytrityl", "trityl" or "DMT") which is conveniently acid labile and is removable under non-adverse conditions. A suitable reagent for detritylation is dichloroacetic acid in dichloromethane.

Since acidic solutions containing the dimethoxytrityl cation are bright orange, the effluent solution may be collected after each detritylation and assayed spectrophotometrically to give the coupling efficiency of the preceding reaction sequence.

(b) The Coupling Step

The coupling step is sensitive to moisture. Accordingly, any water must be removed from the first nucleoside-support before the coupling step. After deblocking, the first nucleoside is dried under vacuum, and preferably, an argon atmosphere is introduced, before the activated second nucleoside ("monomer") is introduced. The $X_1$ substituent of the coupling group preferably comprises a dialkylamino group. Such coupling groups are preferably activated to enhance reaction with the 5'-hydroxyl of the first nucleoside. Tetrazole comprises a suitable activator and acts by protonating the nitrogen atom of the dialkylamino group and also by forming a nucleoside-3'-O-phosphomonotetrazolide via a substitution reaction. Both species will undergo rapid nucleophilic substitution reactions with the 5'-hydroxyl group of the first nucleoside to form an internucleoside trivalent phosphorus linkage.

Thus, in one embodiment, the coupling step may be conducted by mixing an aliquot of second nucleoside (monomer) and an aliquot of tetrazole solution in a dry, argon filled vessel and then injecting the monomer-tetrazole mixture immediately into a vessel containing the deprotected first nucleoside and allowing a reaction time of about three minutes. In the solid-phase process, the coupling mixture (activated monomer) is removed by filtration; then, the support is washed by acetonitrile before proceeding with the oxidizing step.

In order to obtain high coupling efficiencies, typically large excesses of monomer to first nucleoside and activator to monomer have been used. Manufacturers of DNA synthesizers such as Milligen (Biosearch) recommend the use of about 4.8 to about 7.3 equivalents of monomer per equivalent of first nucleoside and from about 10 to about 15 equivalents of activator per equivalent of monomer (effectively from about 48 to about 110 equivalents of activator per equivalent of first nucleoside). Previously, poor coupling efficiencies (about 88 or less) were obtained using these reaction conditions, especially in the synthesis of methylphosphonate oligomers.

According to the process of the present invention, we have found that we can obtain high coupling efficiencies on the order of 95.5% or greater using significantly lower ratios of monomer to first nucleoside and activator to monomer. This finding is especially advantageous in large scale preparation of oligomers, on the order of about 15 μmoles or greater of oligomer. High coupling efficiencies are maintained in preparation of about 120 μmoles or greater of oligomer. In such large scale preparations, not only are the use of large excesses of monomer economically disadvantageous, but also, as noted, poor coupling efficiencies (on the order of about 83%) have been obtained using the manufacturer's recommended reagents and ratios, despite the use of large excesses of monomer and activator. Obtaining a sufficiently high coupling efficiency is especially important in synthesizing oligomers as chain length increases. When an 18 mer is synthesized at an average coupling efficiency of about 83%, the yield is only 4.2%; however, at average coupling efficiencies of about 95.5%, a yield of about 46% is obtained in the synthesis of an 18 mer. Thus, as chain length of the oligomer being synthesized increases, the effect of small differences in coupling efficiencies on overall yield is compounded, so that small increases in coupling efficiency per reaction cycle may result in significant improvements in yield of oligomer. See, in particular, Example 5 and Table IV.

We have found that following the processes of the present invention, high coupling efficiencies may be obtained using from about 1 to about 5, preferably from about 1.5 to about 3, and more preferably from about 2.5 to about 3 equivalents of monomer per equivalent of first nucleoside and from about 2 to about 5, preferably from about 2.2 to about 3 equivalents of activator per equivalent of monomer (effectively from about 2 to about 25, preferably about 3.3 to about 15 and more preferably from about 4.4 to about 8.4 equivalents of activator per equivalent of first nucleoside).

(c) The Oxidizing Step

The relatively unstable trivalent phosphorus of the internucleoside linkage is converted into a stable pentavalent phosphorus linkage by treatment with an oxidizer reagent. This reagent conventionally comprises iodine, tetrahydrofuran, 2,6-lutidine and from at least about 2% to about 25% or more water.

Oxidizer reagents which comprise relatively large amounts of water have been used for oligomer synthesis and are recommended by manufacturers of DNA synthesizers such as Milligen. For example, Milligen, the manufacturer of Biosearch DNA synthesizers, recommends an oxidizer reagent which comprises 2.3 equivalents iodine ($I_2$) and 716 equivalents water per equivalent of internucleoside linkage (i.e. per equivalent first nucleoside), or about 9% water. Commercially available oxidizer reagents have at least about 2% water up to about 25% or more water.

We have surprisingly found that use of low water oxidizer reagents according to the processes of the present invention gives high coupling efficiencies in the coupling step and results in high levels of oxidization of trivalent phosphorus to pentavalent phosphorus to maintain a high overall coupling efficiency. These low water oxidizer reagents contain much less water, from one to two orders of magnitude less water, than the conventionally-used oxidizer reagents. Thus, we have surprisingly found that oxidizer reagents having on the order of from about 0.1% to about 0.5%, water such as reagents in the range of about 0.25% to about 0.18% water (or about 2.2 equivalents water per equivalent first nucleoside) or less, act efficiently and with good oxidizing yields and result in high overall coupling efficiencies. Thus, according to the present invention the trivalent phosphorus internucleoside linkage is oxidized to a pentavalent phosphorus internucleoside linkage using a low water oxidizer reagent which comprises less than about 2% water and at least from about 1 to about 5 equivalents water per equivalent first nucleoside. Preferably, the oxidizer reagent comprises about 100 mM to about 200 mM oxidizing agent and at least about 2 to about 5 equivalents oxidizing agent per equivalent first nucleoside. Suitable oxidizing agents include iodine ($I_2$).

The use of these low water oxidizer reagents which contain significantly lower amounts of water is additionally advantageous because the coupling step is especially water-sensitive, and with use of these low water oxidizer reagents in the oxidizing step, there is less water to be removed before the growing oligomer goes through the coupling step of the next reaction cycle. Thus, use of low water oxidizer reagents in a solid phase process may reduce the washing steps needed to dry the support carrying the growing oligomer chain and, thus, reduce the overall amount of solvent or drying agent required to dry the support.

The oxidizing step is generally complete in less than one minute using a low water oxidizer reagent as described above (which comprises iodine, water, tetrahydrofuran and 2,6-lutidine). In the solid phase process, after oxidation, the support carrying the first nucleoside is washed well with acetonitrile, until it and the effluent (washings) are colorless, before the capping reagent is added.

(d) The Capping Step

The capping step serves to render unreactive any remaining free hydroxyl groups of the first nucleoside which did not react with activated coupling group of the second nucleoside. The capping step ensures that subsequent addition reactions proceed only by propagating chains of the desired nucleoside sequence. In a typical capping step, uncondensed 5'-hydroxyl groups of the first nucleoside (in that reaction cycle) are acetylated by acetic anhydride rendering them inert (or unreactive) towards further chain extension. 4-dimethylaminopyridine (DMAP) is used to catalyze the acetylation reaction.

If added together, it is preferred to mix aliquots of acetic anhydride and DMAP solutions just before use in each cycle because the mixture may darken and deteriorate rapidly. Alternatively, acetic anhydride and DMAP solutions may be added concomitantly. Capping is generally complete in about two minutes or less. Excess capping reagent is removed by filtration; the support is washed with acetonitrile and then with dichloromethane before the start of the next reaction or synthesis cycle.

The use of the capping step, by ensuring that previously uncondensed 5'-hydroxyls are not extended, means that in the deblocking step, the amount of DMT released is directly proportional to the coupling efficiency of the reaction cycle and, accordingly, measurement of the amount of DMT released in the deblocking (or detritylation) step may be used to monitor coupling efficiencies. In addition, excess capping reagent may help to scavenge residual water remaining on the solid support from the oxidizer reagent.

To assist in understanding the present invention, the following examples are included which describe the results of a series of experiments. The following examples relating to this invention should not, of course, be construed as specifically limiting the invention and such variations of the invention, now known or later developed, which would be within the purview of one skilled in the art are considered to fall within the scope of the present invention as hereinafter claimed.

EXAMPLES

Example 1

PREPARATION OF METHYL PHOSPHONATE OLIGOMERS

Sufficient solid support derivatized with 5'-O-DMT-protected nucleoside (which will be at the 3'-end of the oligomer) to give 150 μmoles of that nucleoside is placed in the reactor vessel of a Biosearch 8800 DNA synthesizer. The support is treated with 5×14.6 ml aliquots of 2.5% dichloracetic acid in dichloromethane. The bright orange colored solution is collected for later spectrophotometric analysis to determine coupling efficiencies. The support is then washed with 7×17.5 ml aliquots of dry acetonitrile. To the support is added 4 ml of a 100 mM solution of phosphonamidite monomer (400 μmoles or 2.7 equivalents, or if the added monomer is T, slightly less may be used, about 2.5 equivalents). While the mixture is stirring, tetrazole (1.98 ml, 894 μmoles, 450 mM or 2.24 equivalents with respect to monomer) is added. The mixture is allowed to stir for about three minutes, is filtered and then washed with 2×2.8 ml acetonitrile. To the support 4.06 ml (2.7 equivalents with respect to support loading) of oxidizer (25 g/l $I_2$, 0.18% water, 25% 2,6-lutidine, 74.82% tetrahydrofuran) is added. The mixture is allowed to stir for about one minute and is then filtered and washed with 4×18 ml dry acetonitrile. The material on the support (dinucleotide) is then treated with the concomitant addition of 10 ml CAP A solution (40% acetic anhydride, 60% tetrahydrofuran) and 10 ml CAP B solution (0.625% 4-dimethylaminopyridine in anhydrous pyridine). The mixture is allowed to stir for about one minute and then filtered. The support is washed with 6×18 ml acetonitrile.

For addition of additional nucleoside monomeric units to the growing oligomer chain, the above procedure is repeated, using the appropriate nucleoside monomer until the oligomer of designated length and sequence is synthesized.

Table I depicts a comparison of reagent ratios conventionally used and those used according to the preferred process of the present invention.

Table II lists the coupling efficiencies obtained in synthesizing two methyphosphonate oligomers using this general procedure.

Note: The lot of C monomer used in the syntheses reported in Table II was found to have about 2.5% triethylamine. (Triethylamine is used in the eluant to purify the monomer and is normally removed by the three subsequent co-evaporations with acetonitrile.) The Tetrazole activator is a weak acid and acts as such to activate the monomer and enhance coupling of monomer to support (or oligomer chain). It is believed the residual triethylamine (a base) may have neutralized the tetrazole activator, thereby decreasing coupling. Procedures which normally remove triethylamine in this instance did not adequately remove residual triethylamine.

TABLE I

| | Milligen | Process of Example 1 |
|---|---|---|
| Equivalents Monomer | | |
| A | 5.3 | 2.7 |
| C | 5.3 | 2.7 |
| G | 7.3 | 2.7 |
| T | 4.8 | 2.5 |
| Activator/Monomer | | |
| A | 13 | 2.2 |
| C | 13 | 2.2 |
| G | 10.6 | 2.2 |
| T | 14.6 | 2.2 |
| Oxidizer Equivalents to Initial Chain | | |
| $I_2$ | 2.3 | 2.2 |
| $H_2O$ | 716 | 2.2 |

TABLE II

| OLIGOMER NO. 1 | |
|---|---|
| C - 93.8% | T - 89.9% |
| C - 100.5% | A - 97.3% |
| T - 98.5% | C - 76.6% |
| C - 99.7% | A - 95.9% |
| T - 96.8% | A - 93.8% |
| A - 95.5% | A - 101.0% |
| G - 98.0% | |
| Overall yield: | 54.4% for a pentadecamer |
| Scale: | 150 μmole |
| Average coupling efficiency: | 95.4% |
| OLIGOMER NO. 2 | |
| G - 112.3% | G - 99.6% |
| T - 102.5% | T - 93.3% |
| T - 97.1% | C - 92.2% |
| A - 98.5% | C - 89.6% |
| C - 101.8% | T - 99.5% |
| C - 86.7% | T - 93.8% |
| C - 92.9% | C - 81.4% |
| C - 104.6% | T - 102.6% |
| G - 93.0% | |
| Overall yield: | 46.9% for an octadecamer |
| Scale: | 150 μmole |
| Average Coupling Efficiency: | 95.6% |

Example 2

DERIVATIZATON OF HYDROXYLATED METHACRYLIC POLYMER AS A SOLID SUPPORT FOR DNA SYNTHESIS

Into a 2 liter flask fitted with an overhead stirrer was added hydroxylated methacrylic polymer beads (100 g, 650 A pore size, 40–90 μm particle size) derivatized with epoxide groups (812 μeq/g). To this was added 1,12-dodecanediamine (100 g) and 1 liter of 1,4-dioxane. The mixture was stirred and refluxed for 18 hours. The mixture was then filtered warm and the solids washed with warm dioxane (300 ml). The solid material was washed with dichloromethane and air dried. The solid was suspended in a 2.5% solution of dichloracetic acid in dichloromethane and shaken on a shaker table for 4 hours. The mixture was filtered and washed with dichloromethane. The solid was then washed with a 15% solution of triethylamine in dichloromethane (1 liter) followed by a wash with dichloromethane (300 ml) and finally air dried. A portion of this material (25 g) was suspended in dry pyridine (1250 ml). To this was added 5'-O-dimethyoxytrityl-N-isobutyryl-3'-O-succinyl-2'-deoxyguanosine 1 (4.0 g), ethyl-3(3-dimethylamino)propyl carbodiimide hydrochloride (10.0 g), 4-dimethylaminopyridine (500 mg), and triethylamine (2 ml). The mixture was shaken on a shaker table for 60 hours. The mixture was filtered and washed with pyridine (300 ml), methanol (300 ml), and dichloromethane (300 ml). The material was air dried. The loading of nucleoside on support was determined by measuring trityl release of a small aliquot in 2.5% dichloracetic acid in dichloromethane at 504 nm in a spectrophotometer. The loading in this example was 57.4 μmoles/g.

The material was suspended in acetic anhydride-pyridine (1/1) and 4-dimethylaminopyridine (300 mg) was added. After stirring 4 hours the material was filtered and washed with dichloromethane and air dried. The material was then ready for use on the DNA synthesizer. 1/

1/ Richard T. Pon, Nassim Usman, and Kelvin K. Ogilvie Biotechniques 6: 768–775 (1988).

Example 3

SYNTHESIS OF AN OCTADECAMER ON A 150 µMOLE SCALE USING LOW WATER OXIDIZER REAGENT

Solid support (2.44 g) derivatized with 5'-O-DMT-N-isobutyryl 3'-O-succinyl deoxycytidine (61.5 µmoles/g) was placed in the reactor vessel of a Biosearch 8800 DNA synthesizer. This solid support was treated with 5×14.6 ml aliquots of 2.5% dichloracetic acid in dichloromethane. The bright orange colored solution was collected for later spectrophotometric analysis. The support was then washed with 7×17.5 ml aliquots of dry acetonitrile. To the support was added 4 ml of a solution of N-isobutyryl-5'-O-DMT-2'-O-deoxyguanosine methylphosphonamidite monomer at a concentration of 100 mM (400 µmoles, 2.7 equivalents). While stirring, tetrazole (1.98 ml, 894 µmoles, 450 mM concentration, 2.24 equivalents with respect to monomer) was added. The mixture was allowed to stir for 3 minutes followed by filtration and 2×2.8 ml washes with acetonitrile. Oxidizer (4.06 ml, 2.7 equivalents with respect to support loading, oxidizer=25 g/l $I_2$, 0.18% water, 25% 2,6-lutidine, 74.82% tetrahydrofuran) was added. This was allowed to stir for 1 minute and was subsequently filtered and washed with 4×18 ml of dry acetonitrile. The material on the support was then treated with the concomitant addition of Cap A solution (10 ml, 40% acetic anhydride, 60% tetrahydrofuran) and Cap B solutions (10 ml, 0.625% 4-dimethylaminopyridine in anhydrous pyridine). This mixture was allowed to stir for 1 minute. The mixture was filtered and the support washed with 6×18 ml portion of acetonitrile. At this point the cycle was repeated starting with the removal of the DMT group on the deoxyguanosine nucleoside which had just been added to the deoxycytidine already linked to the support with 2.5% dichloroacetic acid in dichloromethane solution. The 5'-hydroxyl was then free for reaction with the next monomer which was 5'-O-DMT-thymidine. The above process was repeated 15 more times with the appropriate monomer to obtain an oligomer of the sequence: 5'-GTC-TTC-CTG-CCC-CAT-TGC-3'.

Example 4

USE OF THE IMPROVED SYNTHESIS PROCESS TO SYNTHESIZE METHYL PHOSPHONATE OLIGOMERS USING THE MILLIGEN 8800 DNA SYNTHESIZER

The following all methyl phosphonate oligonucleotide octadecamer was prepared on the Milligen 8800 DNA Synthesizer using the improved synthesis protocol:

5'-CCA-CGA-AAG-GCA-TGA-CCG-3'

The synthetic cycle consisted of two programs as follows:

1. Deblocking: Removal of the 5'-O-dimethoxytrityl with dichloroacetic acid. Wash the oligomer with dry acetonitrile to prepare for coupling.
2. Coupling: Couple the desired oligonucleoside to the growing oligomer chain using about 3 equivalents of monomer per equivalent oligomer and 4.5 equivalents of tetrazole per equivalent monomer.
3. Oxidizing: Oxidize using an oxidizer reagent which comprises 0.1M $I_2$ with 0.1M water in tetrahydrofuran/2,6-lutidine.
4. Capping: Cap unreacted 5'-hydroxyl groups with dimethylaminopyridine/acetic anhydride.
5. Return to first step of cycle for next monomer addition.

The programs used with the synthesizer were named MTHL_06 (main) and CPLAW11 (coupling) and were obtained from the manufacturer.

The reagent mixtures used were as follows:
1. Activator: 0.45M tetrazole in acetonitrile.
2. Cap A: 40% acetic anhydride in acetonitrile.
3. Cap B: 0.625% dimethylaminopyridine in pyridine.
4. Deblock: 2.5% dichloroacetic acid in dichloromethane.
5. Oxidizer: 0.1M $I_2$ in tetrahydrofuran/2,6-lutidine/water (74.82/25/0.18:v/v/v).
6. Wash A: acetonitrile containing <30 ppm water.
7. Wash B: acetonitrile containing <30 ppm water.
8. Monomers: all monomers were diluted to 0.1M in acetonitrile
9. Support: The oligomer was synthesized using a support which comprised controlled pore glass beads derivatized with deoxyguanosine.

The average coupling efficiency was 96.7% per cycle based on trityl absorbance observed at 504 nm with a standard deviation of 2.02. The overall yield of oligomer (18 mer) was 56.5%. The coupling efficiency for a monomer was 97.6% (sd-1.35,n=6), for the C monomer was 95.7% (sd-1.85, N=5); for the G monomer at 96.9% (sd-2.55, n=4), and for the T monomer was 95.9% (n=1). Table III lists the coupling efficiencies obtained in each reaction cycle in synthesizing this oligomer.

TABLE III

| Base | Coupling Efficiency |
|---|---|
| G | — |
| C | 113.5% |
| C | 98.5% |
| A | 98.9% |
| G | 98.0% |
| T | 95.9% |
| A | 95.9% |
| C | 94.4% |
| G | 99.1% |
| G | 92.6% |
| A | 95.7% |
| A | 98.5% |
| A | 99.0% |
| G | 98.1% |
| C | 96.0% |
| A | 97.9% |
| C | 93.1% |
| C | 96.6% |

Example 5

COMPARISON OF COUPLING EFFICIENCIES USING USING OXIDIZER REAGENTS HAVING DIFFERENT WATER CONTENTS

Table IV depicts a comparison of coupling efficiencies (C.E.) using oxidizer reagents having water contents ranging from 25% to 0.25% and using low monomer to support (or first nucleoside) ratios.

Oligomers were synthesized using either a Biosearch 8750 or 8800 DNA synthesizer. Reaction cycles were carried out as described previously (see, e.g. Examples 3 and 4) using the noted monomer ratio and oxidizer reagent.

TABLE IV

| Biosearch Instrument | Monomer Ratio | Average Coupling Efficiency | % Water in Oxidizer | Synthesis Scale | Normalized* Yield |
|---|---|---|---|---|---|
| 8750 | ~3.7:1 | 96.2% | 0.25% | 15 µmole | 47.9% |
| 8750 | ~3.7:1 | 95.6% | 2.5% | 15 µmole | 42.5% |
| 8750 | ~3.7:1 | 93.5% | 10% | 15 µmole | 27.9% |

TABLE IV-continued

| Biosearch Instrument | Monomer Ratio | Average Coupling Efficiency | % Water in Oxidizer | Synthesis Scale | Normalized* Yield |
|---|---|---|---|---|---|
| 8750 | ~3.7:1 | 93.8% | 25% | 15 μmole | 29.6% |
| +8750 | 32:1 | 95.4% | 10% | 1 μmole | 40.9% |
| 8800 | ~3:1 | 97.1% | 0.25% | 129 μmole | 57.2% |
| 8800 | ~3:1 | 96.0% | 2.5% | 135 μmole | 46.0% |
| 8800 | ~3:1 | 94.7% | 10% | 135 μmole | 35.5% |

*Normalized to a 20-mer, i.e. 19 couplings at calculated average C.E. (coupling efficiency).
+Standard recommended BioSearch program for phosphodiester synthesis used (including reagents and recommended amounts).

We claim:

1. A process of forming an internucleoside linkage having a pentavalent phosphorus between a 5'-oxygen of a first nucleoside and a 3'-oxygen of a second nucleoside wherein said first nucleoside has a blocking group attached to the 5'-oxygen and is linked by the 3'-oxygen to a support, another nucleoside by a 5'-phosphorus group or an oligomer; and said second nucleoside has a blocking group attached to the 5'-oxygen and a coupling group attached to the 3'-oxygen wherein said coupling group is:

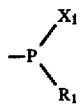

wherein $X_1$ is halogen or substituted amino and $R_1$ is alkyl, aryl, optionally substituted alkoxy or optionally substituted aryloxy; which comprises:

(a) treating said first nucleoside under deblocking conditions to remove the 5'-blocking group and generate a free 5'-hydroxyl group, (b) contacting under activating and coupling conditions said first nucleoside and second nucleoside in the presence of an activator, so that the first nucleoside and second nucleoside are coupled by an internucleoside linkage having trivalent phosphorus group, (c) oxidizing said trivalent phosphorus to a pentavalent phosphorus under oxidizing conditions which include a low water oxidizer reagent comprising iodine as an oxidizing agent and less than about 2% water but at least about 1 to about 5 equivalents of water per equivalent of first nucleoside.

2. A process according to claim 1 wherein said internucleoside linkage having a pentavalent phosphorus is a methyl phosphonate linkage.

3. A process according to claim 1 wherein said oxidizer reagent comprises from about 0.1% to about 0.5% water.

4. A process according to claim 1 further comprising:

(d) capping unreacted 5'-O-hydroxyl groups to render them unreactive.

5. A process according to claim 4 wherein said oxidizer reagent comprises from about 0.1% to about 0.5% water.

6. A process according to claim 4 wherein in step (b) said second nucleoside and said first nucleoside are present in a ratio of from about 1 to 5 equivalents of second nucleoside per equivalent of first nucleoside.

7. A process according to claim 6 wherein said internucleoside linkage having a pentavalent phosphorus is a methyl phosphonate linkage.

8. A process according to claim 6 wherein in step (b) said activator and said second nucleoside are present in a ratio of about 2 to about 5 equivalents activator per equivalent of second nucleoside.

9. A process according to claim 4 further comprising: (e) repeating steps (a) to (d) a sufficient number of times to generate an oligomer having a desired number of nucleosides.

10. A process according to claim 9 wherein in step (b) said second nucleoside and said first nucleoside are present in a ratio of from about 1 to about 5 equivalents of second nucleoside per equivalent of first nucleoside.

11. A process according to claim 10 wherein in step (b) said activator and said second nucleoside are present in a ratio of about 2 to about 5 equivalents of activator per equivalent of second nucleoside.

12. A process according to claim 11 wherein said oxidizer reagent comprises from about 0.1% to about 0.5% water.

13. A process according to claim 12 wherein said internucleoside linkage having a pentavalent phosphorus is a methyl phosphonate linkage.

14. In a process of forming an internucleoside linkage having a pentavalent phosphorus between a 5'-oxygen of a first nucleoside and a 3'-oxygen of a second nucleoside wherein said first nucleoside has a 5'-hydroxyl group and is attached by a 3'-oxygen to a solid support or another nucleoside and said second nucleoside has a blocking group attached to a 5'-oxygen and a coupling group attached to a 3'-oxygen, wherein said first nucleoside and second nucleoside are contacted under coupling and activating conditions in the presence of activator and couple to form an internucleoside linkage having a trivalent phosphorus group, the improvement which comprises adding an oxidizing amount of a low water oxidizer reagent which comprises iodine as an oxidizing agent and less than about 2% water but at least about 1 to about 5 equivalents of water per equivalent of first nucleoside, under oxidizing conditions sufficient to oxidize said trivalent phosphorus group to a pentavalent phosphorus group.

15. A process according to claim 14 wherein said internucleoside linkage having a pentavalent phosphorus is a methylphosphonate linkage.

16. A process according to claim 14 wherein said oxidizer reagent comprises from about 0.1% to about 0.5% water.

17. A process according to claim 14 wherein said oxidizer reagent comprises from about 100 mM to about 200 mM oxidizing agent, and at least about 2 to about 5 equivalents oxidizing agent per equivalent first nucleoside.

18. A process according to claim 17 wherein said oxidizer reagent comprises from about 0.1% to about 0.5% water.

19. A process for the preparation of deoxyribonucleoside phosphate or phosphonate esters of the formula:

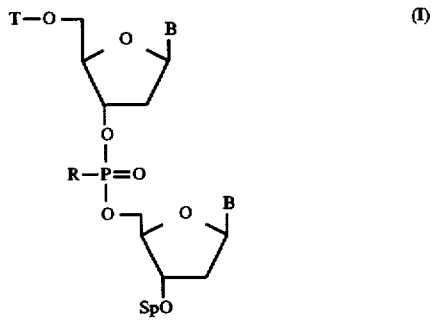

(I)

wherein T is a blocking group for a primary hydroxyl group; B is a base; R is a hydroxy, alkyl, aryl, optionally substituted alkoxy or optionally substituted aryloxy, and Sp is a support or a nucleoside 5'-phosphorus ester of the formula

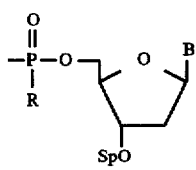

wherein a first nucleoside of the formula:

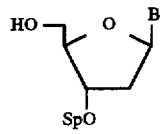

is reacted with a second nucleoside of the formula

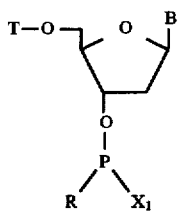

wherein $X_1$ is halogen or substituted amino, in the presence of an activator to give a resulting compound of the formula:

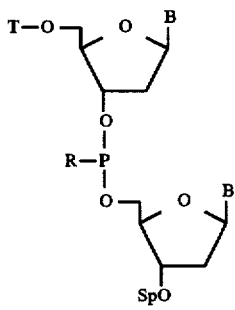

which is oxidatively converted to a compound of formula I in the presence of a low water oxidizer reagent which comprises iodine as oxidizing agent and less than about 2% water but at least from about 1 to about 5 equivalents water per equivalent of compound V.

20. A process according to claim 19 wherein R is alkyl.

21. A process according to claim 19 wherein said oxidizer reagent comprises from about 0.1% to about 0.5% water.

22. A process according to claim 21 wherein R is methyl.

23. A process according to claim 19 wherein said second nucleoside and said first nucleoside are reacted in a ratio of from about 1 to about 5 equivalents of second nucleoside per equivalent of first nucleoside.

24. A process according to claim 23 wherein said oxidizer reagent comprises from about 0.1% to about 0.5% water.

25. A process according to claim 23 wherein said activator is present in a ratio of about 2 to about 5 equivalents of activator per equivalent of second nucleoside.

26. A process according to claim 25 wherein said oxidizing reagent comprises from 100 mM to about 200 mM oxidizing agent and at least from about 1 to about 5 equivalents oxidizing agent per equivalent of compound (V).

27. A process according to claim 26 wherein said oxidizing reagent comprises from about 0.1% to about 0.5% water.

28. A process according to claim 27 wherein R is methyl.

* * * * *